United States Patent
Peña Duque et al.

(10) Patent No.: US 10,973,665 B2
(45) Date of Patent: *Apr. 13, 2021

(54) INTRALUMINAL DEVICES CONFIGURED FOR DIRECTIONAL EXPANSION

(71) Applicants: Marco Antonio Peña Duque, Tepépan Tlalpan (MX); Carlos Vonderwalde, Richmond (CA)

(72) Inventors: Marco Antonio Peña Duque, Tepépan Tlalpan (MX); Carlos Vonderwalde, Richmond (CA)

(73) Assignees: Marco Antonio Pěna Duque, Tlalpan (MX); Carlos Vonderwalde, Richmond (CA)

( * ) Notice: Subject to any disclaimer, the term of this patent is extended or adjusted under 35 U.S.C. 154(b) by 151 days.

This patent is subject to a terminal disclaimer.

(21) Appl. No.: 15/451,793

(22) Filed: Mar. 7, 2017

(65) Prior Publication Data

US 2017/0172777 A1 Jun. 22, 2017

Related U.S. Application Data

(63) Continuation of application No. 13/061,339, filed as application No. PCT/CA2009/001198 on Aug. 27, 2009, now abandoned.

(Continued)

(51) Int. Cl.
*A61F 2/958* (2013.01)
*A61F 2/91* (2013.01)
(Continued)

(52) U.S. Cl.
CPC .............. *A61F 2/958* (2013.01); *A61F 2/856* (2013.01); *A61F 2/91* (2013.01); *A61F 2/915* (2013.01);
(Continued)

(58) Field of Classification Search
CPC ....... A61M 2/95–97; A61M 2025/9505–9665; A61M 25/10–1002;
(Continued)

(56) References Cited

U.S. PATENT DOCUMENTS

| 4,655,771 A | 4/1987 | Wallsten |
| 4,733,665 A | 3/1988 | Palmaz |

(Continued)

FOREIGN PATENT DOCUMENTS

| CA | 2188233 A1 | 10/1997 |
| CA | 2275921 A1 | 7/1998 |

(Continued)

OTHER PUBLICATIONS

International Search Report from corresponding International Patent Application PCT/CA2009/001198 dated Nov. 26, 2009.

(Continued)

*Primary Examiner* — Shaun L David
(74) *Attorney, Agent, or Firm* — Gowling WLG (Canada) LLP

(57) ABSTRACT

Methods and devices useful, for example, in the field of angioplasty and stenting are disclosed. In some embodiments, the methods, devices and kits are configured for directional expansion inside a lumen, for example of a blood vessel obstructed by plaque. In some embodiments, the directional expansion displaces the plaque in a desired direction.

9 Claims, 12 Drawing Sheets

Related U.S. Application Data

(60) Provisional application No. 61/092,561, filed on Aug. 28, 2008.

(51) Int. Cl.

| | | |
|---|---|---|
| *A61F 2/954* | (2013.01) | |
| *A61M 25/10* | (2013.01) | |
| *A61F 2/915* | (2013.01) | |
| *A61F 2/856* | (2013.01) | |
| A61F 2/852 | (2013.01) | |
| A61F 2/97 | (2013.01) | |
| A61F 2/95 | (2013.01) | |

(52) U.S. Cl.
CPC .......... *A61F 2/954* (2013.01); *A61M 25/1002* (2013.01); *A61M 25/104* (2013.01); *A61F 2/852* (2013.01); A61F 2/9522 (2020.05); *A61F 2/97* (2013.01); A61F 2002/91575 (2013.01); A61F 2210/0004 (2013.01); A61F 2250/006 (2013.01); A61M 2025/1059 (2013.01); A61M 2025/1084 (2013.01); A61M 2025/1093 (2013.01)

(58) Field of Classification Search
CPC .. A61M 2025/1043; A61M 2025/1059; A61M 2025/1068; A61M 2025/1081; A61M 25/104; A61M 2025/1004–1097; A61B 17/12022–12195; A61B 17/22; A61B 2017/1205–12127; A61B 2017/22001–22002; A61B 2017/22051–22071; A61B 2017/22081
See application file for complete search history.

(56) References Cited

U.S. PATENT DOCUMENTS

| | | | |
|---|---|---|---|
| 4,739,762 | A | 4/1988 | Palmaz |
| 4,793,359 | A | 12/1988 | Sharrow |
| 4,800,882 | A | 1/1989 | Giantureo |
| 4,893,623 | A | 1/1990 | Rosenbluth |
| 4,907,336 | A | 3/1990 | Giantureo |
| 4,994,071 | A | 2/1991 | MacGregor |
| 5,019,090 | A | 5/1991 | Pinchuk |
| 5,030,227 | A | 7/1991 | Rosenbluth et al. |
| 5,035,706 | A | 7/1991 | Giantureo et al. |
| 5,037,392 | A | 8/1991 | Hillstead |
| 5,147,385 | A | 9/1992 | Beck et al. |
| 5,246,241 | A | 9/1993 | Saab |
| 5,246,421 | A | 9/1993 | Saab |
| 5,334,145 | A | 8/1994 | Ozasa |
| 5,334,146 | A | 8/1994 | Ozasa |
| 5,415,635 | A | 5/1995 | Bagaoisan et al. |
| 5,645,560 | A | 7/1997 | Crocker et al. |
| 5,749,851 | A | 5/1998 | Wang |
| 6,036,697 | A | 3/2000 | DiCaprio |
| 6,063,092 | A | 5/2000 | Shin |
| 6,296,660 | B1 | 10/2001 | Roberts et al. |
| 6,726,713 | B2 | 4/2004 | Schaldach et al. |
| 6,878,160 | B2 * | 4/2005 | Gilligan .............. A61F 2/86 623/1.12 |
| 6,951,569 | B2 | 10/2005 | Nohill et al. |
| 7,198,632 | B2 | 4/2007 | Lim et al. |
| 7,753,926 | B1 | 7/2010 | Pacetti |
| 2002/0052640 | A1 * | 5/2002 | Bigus .................. A61F 2/07 623/1.11 |
| 2002/0082553 | A1 * | 6/2002 | Duchamp ......... A61M 25/1034 604/103.06 |
| 2003/0233115 | A1 * | 12/2003 | Eversull ............. A61M 25/104 606/194 |
| 2004/0243216 | A1 * | 12/2004 | Gregorich ............ A61F 2/91 623/1.15 |
| 2005/0209674 | A1 * | 9/2005 | Kutscher ......... A61M 25/1002 623/1.11 |
| 2006/0004323 | A1 | 1/2006 | Chang et al. |
| 2008/0215036 | A1 | 9/2008 | Vogel et al. |

FOREIGN PATENT DOCUMENTS

| | | |
|---|---|---|
| CA | 2383304 A1 | 3/2001 |
| CA | 2422691 A1 | 4/2002 |
| CA | 2731976 | 4/2013 |
| CA | 2791086 | 5/2014 |
| CN | 200980133720.2 | 4/2015 |
| EP | 2382522 B1 | 12/2017 |
| ES | 266294673 | 4/2018 |
| IL | 211364 A | 5/2016 |
| IN | 303549 | 11/2018 |
| JP | 9-503945 A | 4/1997 |
| JP | 2001-517483 A | 10/2001 |
| JP | 2002-520095 A | 7/2002 |
| JP | 2003-509158 A | 3/2003 |
| JP | 2004-512867 A | 4/2004 |
| JP | 2004-520880 A | 7/2004 |
| JP | 2004-528066 A | 9/2004 |
| JP | 2006-502799 A | 1/2006 |
| JP | 2007-512908 A | 5/2007 |
| JP | 5733759 B2 | 4/2015 |
| KR | 10-2014-0049093 | 4/2014 |
| MX | 341600 | 8/2016 |
| WO | WO 95/11055 | 4/1995 |
| WO | WO 1997/017101 A1 | 5/1997 |
| WO | WO 99/15108 | 4/1999 |
| WO | WO 00/02598 | 1/2000 |
| WO | WO 01/021109 A1 | 3/2001 |
| WO | WO 02/28317 A2 | 4/2002 |
| WO | WO 02/49703 A2 | 6/2002 |
| WO | WO 02/060345 A2 | 8/2002 |
| WO | WO 2002/060345 A2 | 8/2002 |
| WO | WO 2004/035127 A1 | 4/2004 |
| WO | WO 2005/053937 A1 | 6/2005 |

OTHER PUBLICATIONS

Written Opinion (Form PCT/ISA/237) for corresponding International Patent Application PCT/CA2009/001198 dated Nov. 26, 2009.

International Preliminary Report on Patentability from corresponding International Patent Application PCT/CA2009/001198.

Examiner's Report from related Canadian Patent Application 2,731,976.

* cited by examiner

FIG. 7A
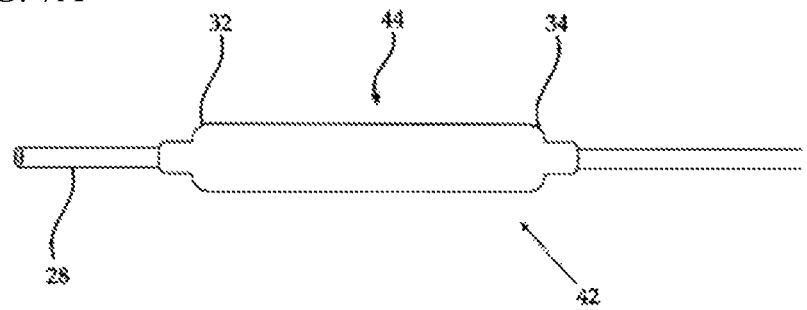
FIG. 7B
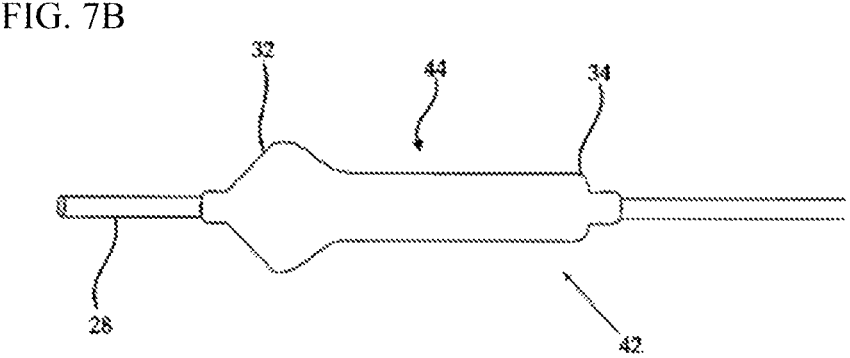
FIG. 7C
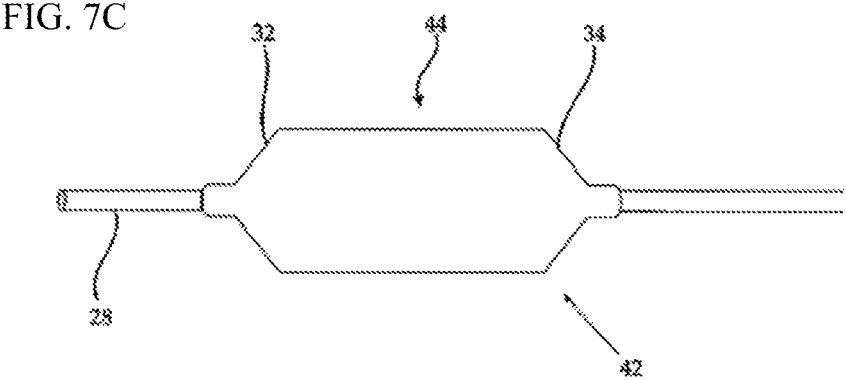
FIG. 7

FIG. 9A
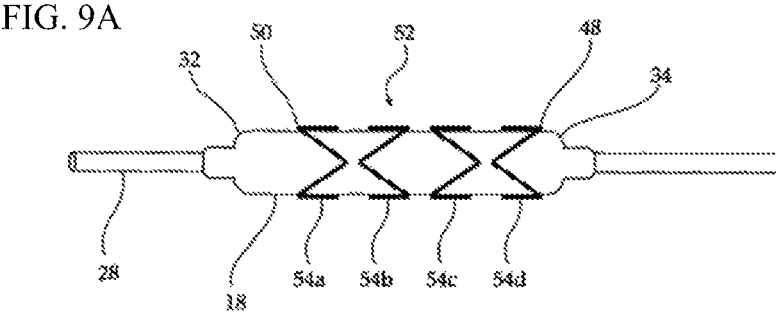
FIG. 9B
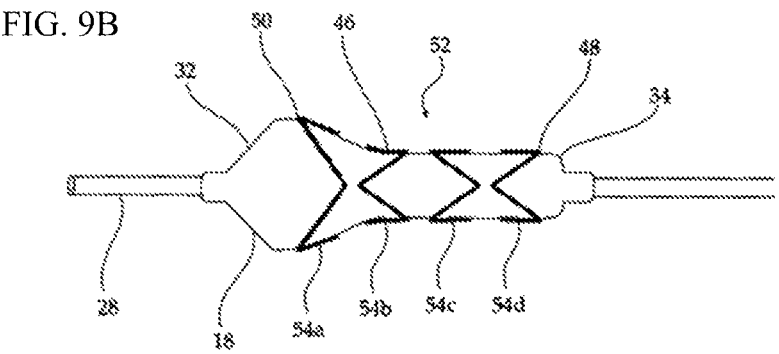
FIG. 9C
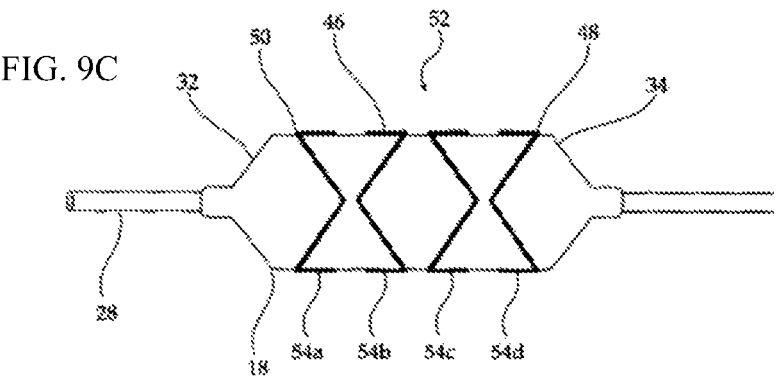
FIG. 9

FIG. 11A
FIG. 11B
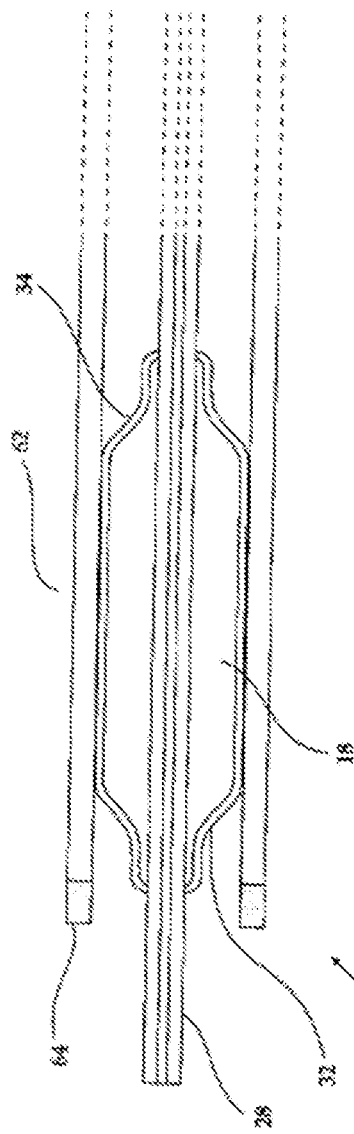
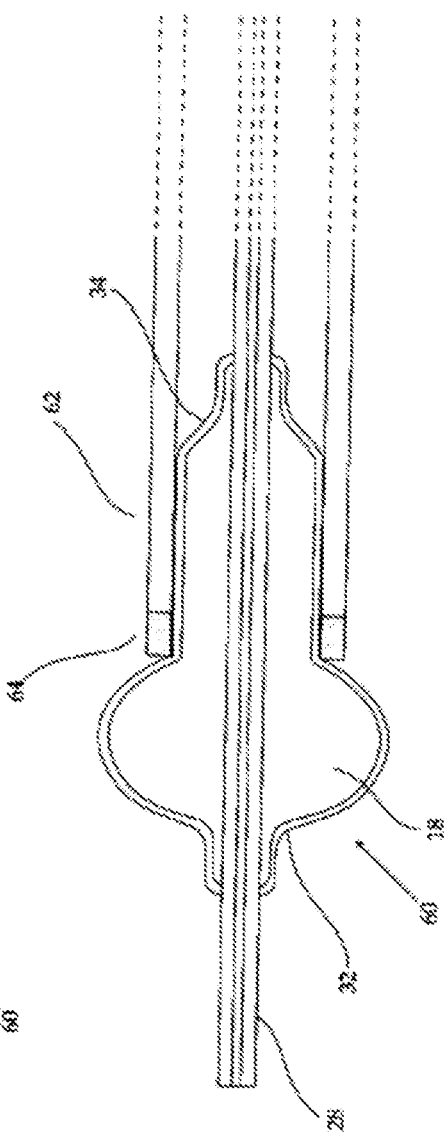
FIG. 11

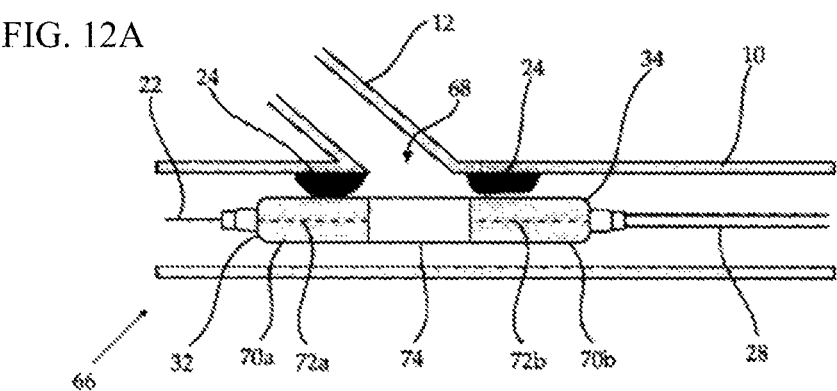
FIG. 12A
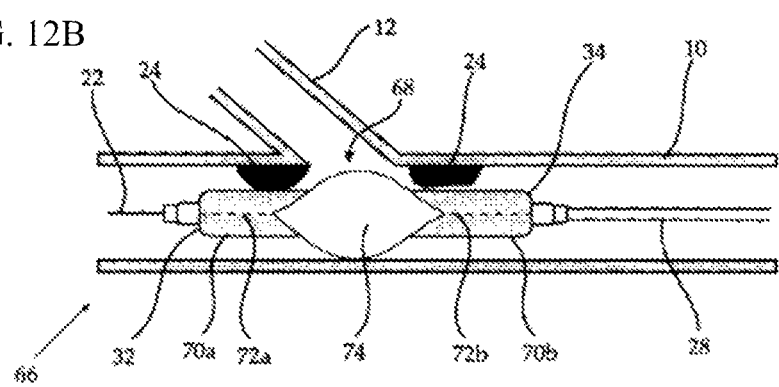
FIG. 12B
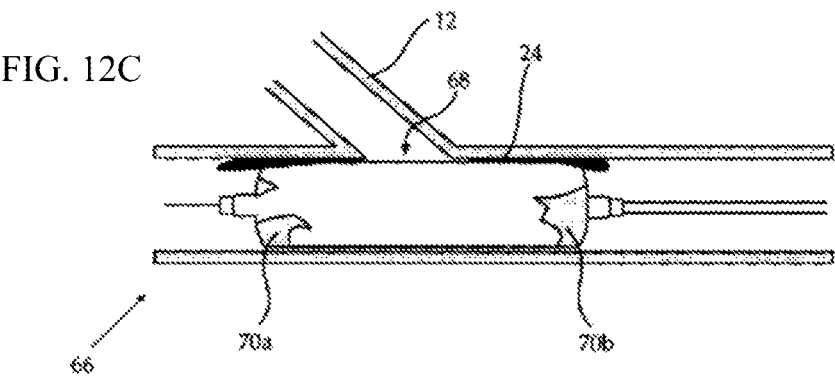
FIG. 12C
FIG. 12

INTRALUMINAL DEVICES CONFIGURED FOR DIRECTIONAL EXPANSION

RELATED APPLICATION

This application is a continuation of application Ser. No. 13/061,339 filed on Apr. 21, 2011 which claims priority from U.S. Provisional Patent Application No. 61/092,561 filed on 28, 2008.

FIELD AND BACKGROUND OF THE INVENTION

The present invention relates to intraluminal medical devices. In some embodiments, the invention relates to expandable devices such as angioplasty balloons and balloon-expandable stents that are configured for directional expansion, for example from a distal end of the device to a proximal end of the device or from a proximal end of the device to a distal end of the device.

Many illnesses are characterized or lead to narrowing or obstruction of the lumen of blood vessels, for example lesions such as plaque deposition, resulting in restricted flow of blood to critical parts of the body such as the heart and the brain.

Balloon angioplasty is a technique used to dilate a region of a lumen of a blood vessel that is narrowed or obstructed with the help of an inflatable catheter-borne balloon. A guide wire is maneuvered into the blood vessel from an incision in the skin past the region of the blood vessel. The catheter is guided along the guide wire so that the balloon is at the region. The balloon is inflated, usually by the introduction of a fluid such as saline through the catheter. The balloon applies an outwards force to the luminal walls of the blood vessel dilating the blood vessel. In some instances, soft/pliable deposits such as plaque are smeared over a large area of the blood vessel wall, dilating the blood vessel lumen. Types of angioplasty include peripheral angioplasty, also known as percutaneous transluminal angioplasty (PTA), involving opening of blood vessels other than the coronary arteries; percutaneous transluminal coronary angioplasty (PCTA), used to treat stenotic coronary arteries; renal artery angioplasty; carotid angioplasty; and cerebral artery angioplasty.

In some cases, a stent is deployed together with balloon angioplasty.

A stent is a device deployed inside a lumen of a bodily vessel to physically maintain patency of the vessel by application of an outwards radial force on the luminal walls of the vessel. Typical vessels treated with stents include respiratory ducts, gastrointestinal ducts, lymphatic ducts, blood vessels and especially arteries that are occluded, stenosed, aneurysmatic, physically damaged, diseased, collapsing or weakened.

Stents are outwardly radially expandable, having a substantially tubular shape both in an unexpanded state with a small radial dimension and in any one of the expanded states with larger radial dimensions. Various constructions of stents are known including rolled-up sheets, slotted or otherwise cut-out tubes and bent wires. Such stents have been disclosed, for example, in U.S. Pat. Nos. 4,655,771; 4,733,665; 4,739,762; 4,800,882; 4,907,336; 4,994,071; 5,019,090; 5,035,706; 5,037,392; and 5,147,385.

For deployment inside a lumen of a bodily vessel an expandable stent is placed in an unexpanded state on a deployment catheter, inserted through an incision in the skin and maneuvered through the body to the deployment location. The stent is then radially expanded to an appropriately-sized expanded state so as to engage the inner walls of the treated vessel. Expandable stents are generally expanded from the unexpanded state to an expanded state using an expansion device, typically a catheter-borne balloon. When the stent is at the deployment location, the expansion device is activated inside the bore of the unexpanded stent to exert an outwards radial force on the inside of the stent, causing the stent to expand to the appropriately-sized expanded state.

In some instances, a stent is deployed subsequently to balloon angioplasty. That said, more commonly a stent is mounted on an angioplasty balloon and angioplasty and stent deployment are performed simultaneously.

Generally, stents are deployed to physically support a blood vessel that has been treated by angioplasty, to prevent vessel collapse.

In some cases a drug-eluting stent is deployed in a blood vessel. In addition to physically supporting the blood vessel, a drug-eluting stent includes an active pharmaceutical ingredient that has a beneficial effect, for example reduces restenosis or increases the rate of healing. Commercially-available drug-eluting stents are exemplified by TAXUS®, EXPRESS²®, ATOM®, and the like (TAXUS, EXPRESS², and ATOM, are registered trademarks of Boston Scientific Scimed Inc., Maple Grove, Minn., USA).

In some cases a covered stent is deployed in a blood vessel. A covered stent includes a cover (also called a jacket) on a luminal and/or outer surface of the stent, covering all or some of the stent body. A stent cover is fashioned from any suitable material including artificial materials (e.g., polymers such as PTFE) and natural materials (e.g., harvested tissue). A stent cover may be configured for various functions including administration of an active pharmaceutical ingredient, functioning as a blood vessel prosthesis, functioning to physically reinforce the blood vessel, functioning to prevent subsequent deposition of plaque, prevention of blood vessel-bursting if physical damage is caused to the blood vessel during balloon-inflation and trapping plaque between the blood vessel wall and the stent cover.

As is known to one skilled in the art, many bodily vessels are bifurcated. By "bifurcated" is meant an object that splits into two branches along a length of the object. A bifurcated blood vessel is depicted in FIG. 1 including a trunk vessel 10 from which a branch vessel 12 branches downstream from a bifurcation point 14. Generally, but not necessarily, the lumen of branch vessel 14 is smaller than that of trunk vessel 12.

A number of systems (depicted in FIG. 2) have been developed for classification of bifurcation lesions, including the Duke classification (FIG. 2A), the Institut Cardiovasulaire Paris Sud classification (FIG. 2B), and the Medina classification (FIG. 2C). For the Medina classification, bifurcation lesions are divided into three segments: proximal segment of the trunk vessel, distal segment of the trunk vessel, and branch vessel. Any involvement of a lesion in each segment will receive the suffix 1, otherwise suffix 0 is assigned. Hence, for example, lesion 1,0,1 means that proximal segment of trunk vessel, and branch vessel are diseased but the distal part of the trunk vessel is free of disease.

In FIG. 3, a number of different techniques used for treatment of obstructed bifurcations (i) are shown: stent+PTCA (ii) including deployment of a stent in the trunk vessel and angioplasty in the branch vessel; T-stenting (iii) including deployment of a first stent in the branch vessel followed by deployment of a second stent in the trunk vessel; reverse T-stenting (iv) including deployment of a first stent in the trunk vessel followed by deployment of a second stent in the branch vessel through an aperture in the wall of the first stent; culotte stenting (v) including deployment of a first stent in the trunk vessel followed by deployment of a second stent from the trunk vessel into the branch vessel through an aperture in the wall of the first stent so that the proximal portions of the stents overlap; V-stenting (vi) where guidewires are placed in the trunk and branch vessel and stents sequentially deployed in each of the vessels or Y-stenting, wherein following V-stenting, the guidewire is removed from the branch vessel and a third stent advanced over the guidewire in the trunk vessel and deployed just at the proximal border of the branch vessel; crush stenting (vii) where two stents are positioned in the bifurcation with the branch vessel stent overlapping into the trunk branch; and kissing stents (viii), wherein stents are placed in both the trunk and branch vessel with the proximal stent portions in parallel.

One of the major problems associated with treatment of bifurcations is the "snow plow" effect, illustrated in FIG. 4A for a proximal lesion, and FIG. 4B for a distal lesion of plaque buildup 16. During the process of expansion of an angioplasty balloon 18 or a stent 20, plaque-shift occurs, redistributing plaque 16 from trunk vessel 12 at least partially into branch vessel 14, obstructing branch vessel 14.

Another major problem, for example as may occur during acute myocardial infarction (AMI) is that expansion of an angioplasty balloon (with or without a stent) may cause plaque or a thrombus to migrate to an undesired location, for example downstream into a narrow section of an artery, possibly obstructing blood flow and making retrieval or management of the plaque or thrombus difficult.

It would be highly advantageous to have an intraluminal medical device useful for deployment in the vasculature, including bifurcated but also not-bifurcated vessels, which is devoid of at least some of the disadvantages of the prior art.

SUMMARY OF THE INVENTION

Some embodiments of the invention relate to intraluminal medical devices such as angioplasty balloon catheters and balloon-expandable stents and methods of using the same that have advantages over known such intraluminal medical devices. Specifically, some embodiments of the invention overcome or reduce the negative consequences of plaque shifting during expansion of an angioplasty balloon or stent, the "snow plow" effect, especially effects such as blocking of a branching vessel.

Specifically, an aspect of some embodiments of the invention is controlled, directional expansion of an intraluminal medical device such as a balloon catheter or balloon-expandable stent, such that during expansion material such as plaque or thrombi is directed in a specific direction (as desired by an operator), for example, away from the side branch of a bifurcated blood vessel, away from a narrowing in a blood vessel or towards an embolic protection device.

According to an aspect of some embodiments of the invention there is provided an expandable intraluminal medical device selected from the group consisting of a balloon catheter and a balloon-expandable stent, the device having a proximal end, a distal end, and a central section, wherein the device is configured for controlled directional expansion within the lumen of a blood vessel.

According to an aspect of some embodiments of the invention, there is also provided a method of performing an angioplasty procedure, comprising: a) introducing into the lumen of a blood vessel an expandable intraluminal medical device selected from the group consisting of a balloon catheter and a balloon-expandable stent, the device having a proximal end, a distal end, and a central section, wherein the device is configured for controlled directional expansion within the lumen; and b) directionally expanding the device within the lumen. In some embodiments, the angioplasty is selected from the group consisting of peripheral angioplasty, percutaneous transluminal coronary angioplasty, renal artery angioplasty, carotid angioplasty, and cerebral artery angioplasty.

In some embodiments, the directional expansion is selected from the group consisting of expansion from the distal end towards the proximal end; expansion from the proximal end towards the distal end; expansion from the proximal end and the distal end towards the central section; and expansion from the central section towards the proximal end and the distal end.

In some embodiments, the device is configured to provide a varying resistance to expansion along the length of the device. As a result, when expansion occurs, the regions of lesser resistance to expansion expand before the regions of greater resistance to expansion.

In some embodiments, the device comprises a balloon where the thickness of balloon material varies along the length of the balloon, the varying thickness providing a varying resistance to expansion: thinner material providing lesser resistance to expansion and thicker material providing greater resistance to expansion. In some embodiments, the balloon has two substantially equally tapered ends. In some embodiments, the thickness of balloon material at the distal end of the balloon is less than a thickness of balloon material at the proximal end of the balloon, so that the balloon tends to directionally expand from the distal end to the proximal end. In some embodiments, the thickness of balloon material at the proximal end of the balloon is less than a thickness of balloon material at the distal end of the balloon, so that the balloon tends to directionally expand from the proximal end to the distal end. In some embodiments, the thickness of balloon material at the distal and proximal ends of the balloon is less than a thickness of balloon material near the central section of the balloon, so that the balloon tends to directionally expand from the distal and proximal ends towards the central section. In some embodiments, the thickness of balloon material near the central section of the balloon is less than the thickness of balloon material at the distal and proximal ends of the balloon, so that the balloon tends to directionally expand from the central section towards the distal and proximal ends.

In some embodiments, the device comprises a balloon having a more tapered end and a less tapered end. In some embodiments, the less tapered end has a substantially rectilinear cross section (e.g., having interior angles of between about 80° and about 100°). In some embodiments, the more tapered end comprises the distal end, such that the resistance to expansion increases from the distal end to the proximal end. In some embodiments, the more tapered end comprises the proximal end, such that the resistance to expansion increases from the proximal end to the distal end. In some embodiments, the thickness of balloon material at the more tapered end is less than a thickness of balloon material at the less tapered end. In some embodiments, such varying thickness allows that the resistance is less at the more tapered end than at the less tapered end, substantially as described above.

In some embodiments, the device comprises a balloon-expandable stent crimped onto a balloon with a varying crimping force along the length of the stent. In some embodiments, the crimping force increases from the distal end to the proximal end, such that the directional expansion occurs from the distal end to the proximal end. In some embodiments, the crimping force increases from the distal end and the proximal end to the central section, such that the directional expansion occurs from the distal end and the proximal end to the central section. In some embodiments, the crimping force increases from the distal end and the proximal end to the central section, such that the directional expansion occurs from the distal end and the proximal end to the central section. In some embodiments, the crimping force increases from central section to the distal end and the proximal end, such that the directional expansion occurs from the central portion to the distal end and the proximal end.

In some embodiments, the device comprises a balloon-expandable stent crimped onto a balloon with a varying crimping temperature along the length of the stent. In some embodiments, the crimping temperature increases from the proximal end to the distal end, such that the directional expansion occurs from the proximal end to the distal end. In some embodiments, the crimping temperature increases from the distal end to the proximal end, such that the directional expansion occurs from the distal end to the proximal end. In some embodiments, the crimping temperature increases from the distal end and the proximal end to the central section, such that the directional expansion occurs from the distal end and the proximal end to the central section. In some embodiments, the crimping temperature increase from central section to the distal end and the proximal end, such that the directional expansion occurs from the central portion to the distal end and the proximal end.

In some embodiments, wherein the device comprises a balloon-expandable stent, the stent comprises a lesser amount of material at a section to be expanded first. In some such embodiments, the lesser amount of material comprises fewer stent struts. In some such embodiments, the lesser amount of material comprises thinner stent struts. In some such embodiments, the lesser amount of material is situated at the proximal end and increases towards the distal end, such that expansion of the stent occurs from the proximal end towards the distal end. In some such embodiments, the lesser amount of material is situated at the distal end and increases towards the proximal end, such that expansion of the stent occurs from the distal end towards the proximal end. In some such embodiments, the lesser amount of material is situated at the proximal end and the distal end, and increases towards the central portion, such that expansion of the stent occurs from the proximal end and the distal end towards the central portion. In some such embodiments, the lesser amount of material is situated at the central portion and increases towards the proximal end and the distal end, such that expansion of the stent occurs from the central portion towards the proximal end and the distal end.

In some embodiments, the intraluminal device further comprises an externally-placed expansion-preventing element.

In some embodiments, the externally-placed expansion-preventing element comprises a removable, non-expandable sheath. In some such embodiments, the removable sheath is removed by pulling from the distal end towards the proximal end of the device, such that expansion occurs from the distal end to the proximal end. In some such embodiments, the removable sheath is removed by pushing from the proximal end towards the distal end of the device, such that expansion occurs from the proximal end to the distal end.

In some embodiments, the externally-placed expansion-preventing element comprises a longitudinal coil having a varying amount of strength along its length, such that a varying amount of resistance is provided to the opening of the intraluminal device.

In some embodiments, the externally-placed expansion-preventing element comprises a degradable element positioned so as to cause constriction of at least a section of the intraluminal device, such that expansion of the constricted section occurs upon degradation of the degradable element. In some embodiments, the degradable element is selected from the group consisting of a heat degradable element, a biologically degradable element, a pH-degradable element and an enzymatically degradable element.

In some embodiments, the externally-placed expansion preventing element comprises a frangible element positioned so as to cause constriction of at least a section of the intraluminal device, such that expansion of the constricted section occurs upon breaking of the degradable element.

According to an aspect of some embodiments of the invention there is also provided the use of the device or method described herein, wherein the directional expansion leads to displacement of plaque in a desired direction.

Unless otherwise defined, all technical and scientific terms used herein have the same meaning as commonly understood by one of ordinary skill in the art to which the invention belongs. In addition, the descriptions, materials, methods and examples are illustrative only and not intended to be limiting. Methods and materials similar or equivalent to those described herein can be used in the practice or testing of the present invention. Generally, the nomenclature used herein and the laboratory procedures utilized in the present invention include techniques from the fields of medicine, biology, chemistry, material sciences, pharmacology, and engineering. Such techniques are thoroughly explained in the literature.

As used herein, the terms "comprising", "including" and "having" or grammatical variants thereof are to be taken as specifying the stated features, integers, steps or components but do not preclude the addition of one or more additional features, integers, steps, components or groups thereof. This term encompasses the terms "consisting of and "consisting essentially of".

Herein the term "proximal" generally refers to the side or end of an elongated medical device such as a catheter or stent that is or is intended to be closer to the performing medical personnel while the term "distal" generally refers to the side or end of an elongated medical device such as a catheter or stent that is or is intended to be further from the performing medical personnel.

BRIEF DESCRIPTION OF THE FIGURES

Some embodiments of the invention are herein described with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIGS. 7A to 7C depict stages of the directional expansion of an embodiment of the invention, a symmetrical angioplasty balloon having varying material thickness;

FIGS. 9A to 9C depict stages of the directional expansion of a stent axially-asymmetrically crimped onto an angioplasty balloon;

FIGS. 11A and 11B depict an embodiment of the invention, comprising an angioplasty balloon having a removable sheath as an external expansion-preventing element, in the unexpanded (11A) and expanded (11B) configuration; and FIGS. 12A to 12C depict stages in the directional expansion of an embodiment of the invention comprising an angioplasty balloon having two tearable bands as frangible expansion-preventing element.

DESCRIPTION OF SOME EMBODIMENTS OF THE INVENTION

Figure 1:
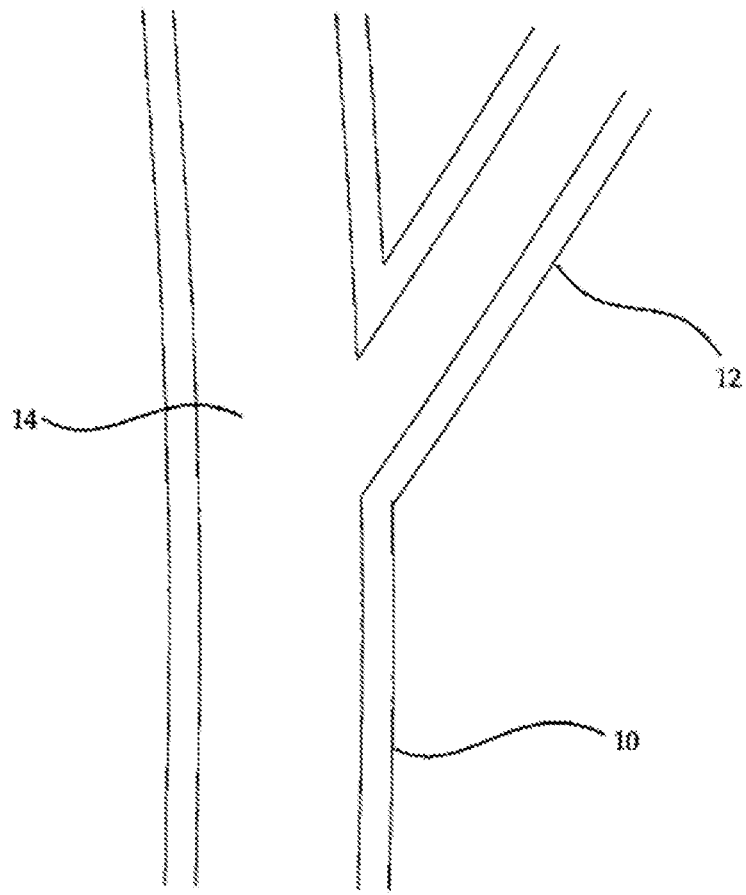
FIG. 1 depicts a bifurcated blood vessel.

The present invention relates to an expandable intraluminal device, such as a balloon catheter or a balloon-expandable stent, which is configured for controlled directional expansion within the lumen of a blood vessel, and methods of use thereof.

The principles, uses and implementations of the teachings of the invention may be better understood with reference to the accompanying description and figures. Upon perusal of the description and figures present herein, one skilled in the art is able to implement the teachings of the invention without undue effort or experimentation. In the figures, like reference numerals refer to like parts throughout.

Before explaining at least one embodiment of the invention in detail, it is to be understood that the invention is not limited in its application to the details set forth herein. The invention can be implemented with other embodiments and can be practiced or carried out in various ways. It is also understood that the phraseology and terminology employed herein is for descriptive purpose and should not be regarded as limiting.

The principle of operation of some embodiments of the invention consists in achieving a controlled directional expansion of an intraluminal device within a lumen of a blood vessel. In some embodiments, the controlled directional expansion is implemented using the principle that expansion of an object generally occurs first in areas of lower resistance to expansion. In some embodiments, the controlled directional expansion allows material such as intraluminal plaque to be displaced in a desired direction, for example away from a branch vessel to avoid obstruction of the branch vessel by displaced plaque.

In some embodiments, the invention provides a directionally-expandable intraluminal medical device such as a balloon catheter or a balloon-expandable stent, having a proximal end, a distal end, and a central section, wherein the device is configured for controlled directional expansion within the lumen of a blood vessel. Generally, one or more components of such a device comprise one or more markers visible with a medical imaging modality allowing correct placement of the device inside a body when used. Examples of suitable markers include those visible in one or more of Ultrasound, X-ray, CT, and MRI imaging modalities.

As used herein, the term "expandable stent" refers to a stent configured for radial expansion upon application of a sufficient outwards radial force on the luminal surface of the stent.

In some embodiments, a stent for implementing the present invention comprises any balloon-expandable stent, such as, for example, a bare metal stent, a drug-eluting stent, a covered stent and/or a coated stent, and as discussed below, a balloon-expandable stent functioning as a framework of an artificial valve.

It is known in the art to deploy a covered stent. Substantially any stent cover known to one skilled in the art is useful for covering a stent used in implementing the teachings of the invention, including internal and external covers, full or partial covers and of any suitable material or combination of materials including natural and artificial materials.

It is known in the art to deploy a coated stent. Many different coatings are known in the art, for example, anti-thrombogenic coatings, anti-angiogenic coatings, anti-coagulant coatings and active pharmaceutical ingredient delivering coatings. Substantially any stent coating known to one skilled in the art is useful for coating one, some or all components of a stent used in implementing the teachings of the invention.

It is important to note that the unexpanded diameter of a stent be as small as possible to ease navigation through the bodily lumen to the deployment location, but the unexpanded diameter must be large enough to allow threading of the stent onto a deployment catheter and the associated stent-expanding device such as a stent-expanding balloon. Any given stent has a wide range of expanded diameters larger than a respective unexpanded diameter. The expanded diameter of a stent subsequent to deployment is determined by the user of the stent according to medical criteria including the natural size of the lumen of the vessel in which the stent is deployed. Most balloon-expandable stents are characterized by a maximal expansion that is the greatest extent to which the stent is expandable without comprising the structural integrity thereof.

In some embodiments, the devices and methods of the invention are used for the treatment of lesions in bifurcated vessels.

In some embodiments, the invention provides a method of performing an angioplasty procedure, comprising introducing into the lumen of a blood vessel an expandable intraluminal medical device, such as a balloon catheter or a balloon-expandable stent, having a proximal end, a distal end, and a central section, wherein the device is configured for controlled directional expansion within the lumen; and directionally expanding the device within the lumen.

The directional expansion may occur, for example, from the distal end to the proximal end, from proximal end to distal end, from the center of the device to its ends or from the ends of the device to its center. The controlled expansion enables control of the direction in which plaque is displaced, for example, in the case of bifurcated vessels inside a trunk vessel such that displacement in the direction of a branch vessel is reduced or prevented.

Figures 2A, 2B:
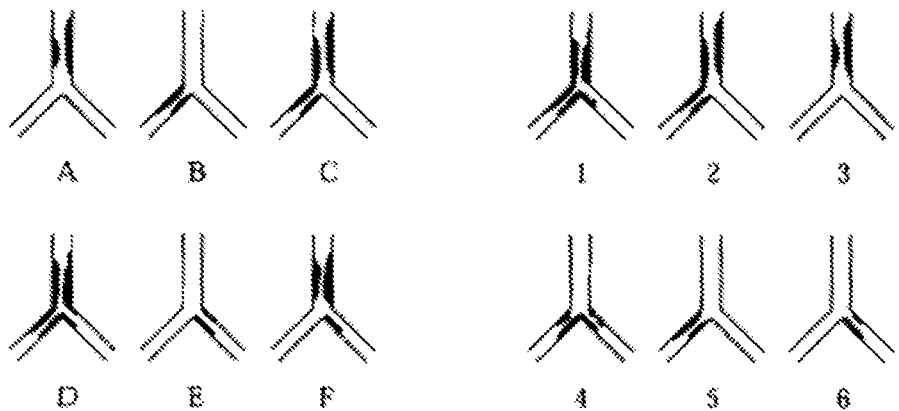
FIGS. 2A to 2C (prior art) depict classifications of atherosclerotic lesions as characterized by the distribution of plaque around a bifurcation of a blood vessel.
Figure 2C:
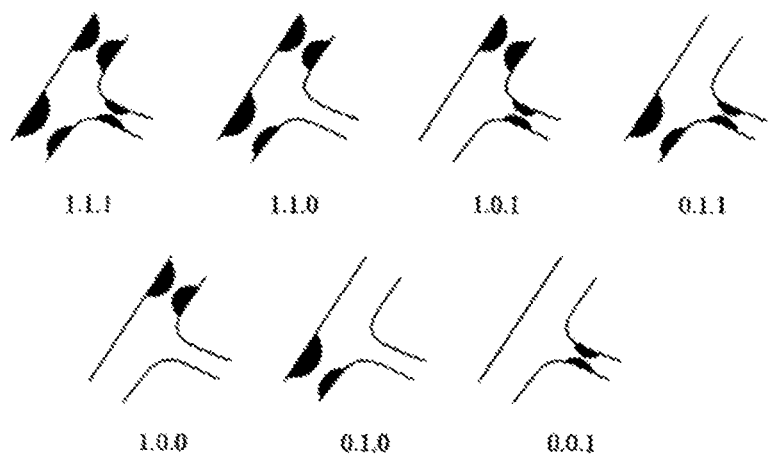
Figure 3:
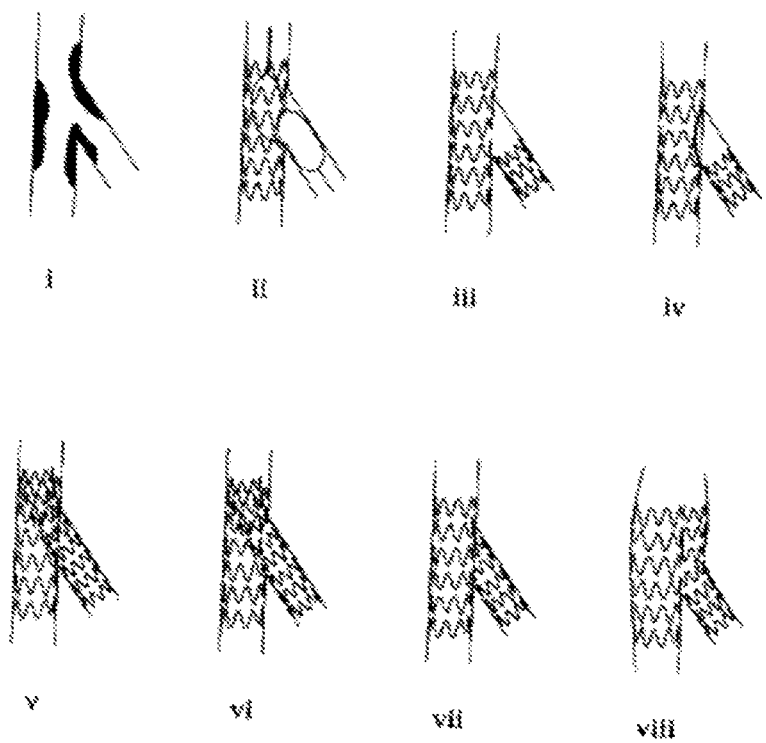
FIG. 3 (prior art) depicts methods of deploying stents in bifurcated vessels.
Figure 4A:
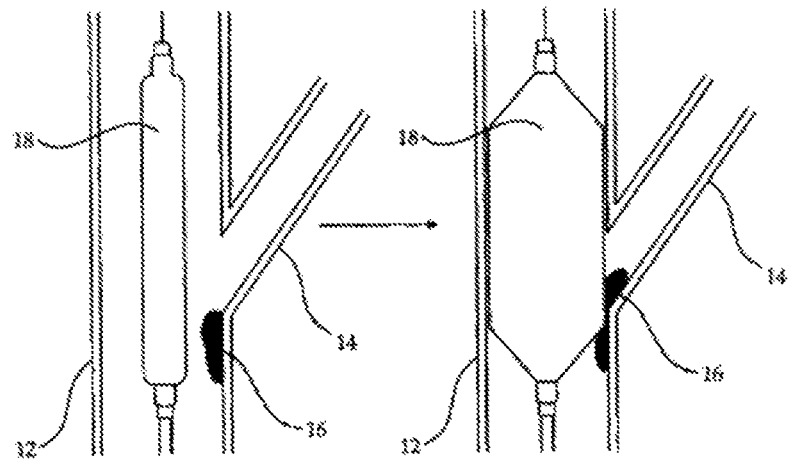
FIGS. 4A and 4B (prior art) depict the "snow plow" effect during angioplasty and stent deployment.
Figure 4B:
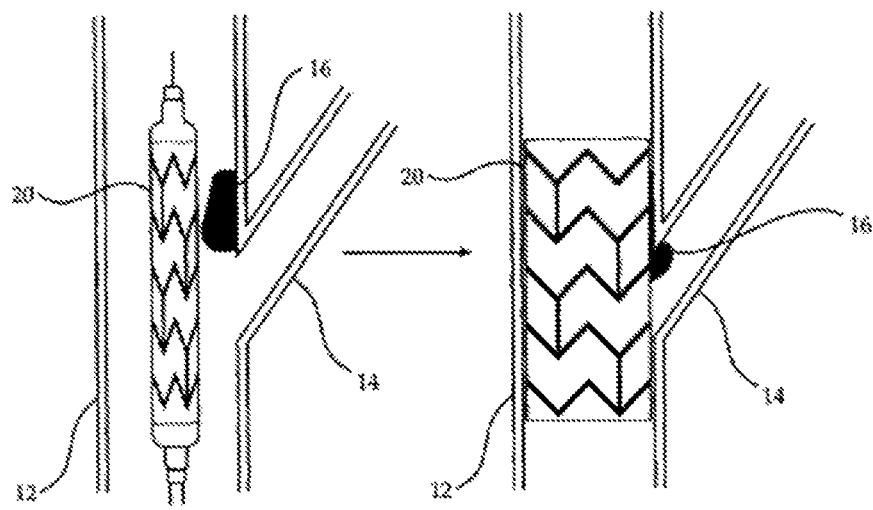
Figure 5:
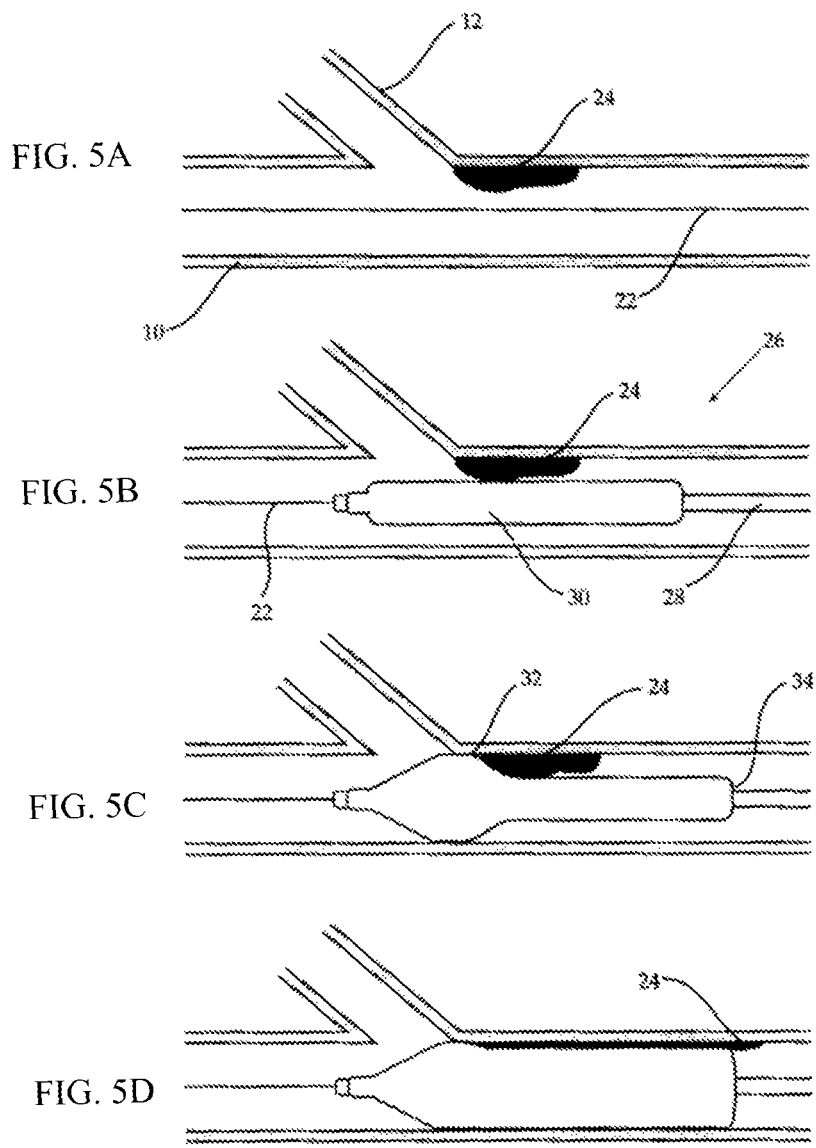
FIGS. 5A to 5D depict the principles of operation of some embodiments of the invention during angioplasty.

In some embodiments, the devices and methods of the invention are used to treat lesions classified as 1.0.0, 0.1.0, 0.0.1 and 1.1.0 in the Medina classification system (see FIG. 2C). For example, in some embodiments, lesion 1.0.0, having the plaque in its proximal segment is treated with a balloon/stent that will inflate/deploy from the distal end to the proximal end, pushing the plaque away from the ostium of the branch vessel. The opposite applies for lesion 0.1.0 where inflation/deployment from proximal end to distal end will, in some embodiments, be preferred.

In some embodiments, a device of the invention is used or a method of the invention is performed in a manner analogous to the known in the art. A guidewire is navigated through the body from an incision in the skin into the vasculature. The guidewire is maneuvered, as known in the art, through a trunk vessel to proximity of the region to be treated, for example the bifurcation point to a side branch. A device (e.g., a balloon catheter, with or without a balloon-expandable stent mounted thereon) configured for directional expansion is mounted on and advanced along the guidewire and thus navigated through the body to be positioned at the proper location in the trunk vessel. Once properly positioned, the expandable device is directionally expanded from one part of the device towards another applying sufficient force to displace plaque in a desired direction, for example, away from a side branch.

Referring now to FIGS. 5A-5D, the principles of operation of some embodiments of methods and intraluminal devices of the invention are shown.

FIG. 5A shows a bifurcated blood vessel having a trunk 10 and branch vessel 12, in which a catheter guidewire 22 is positioned. A plaque lesion 24 is present on an inner luminal wall of trunk vessel 10, proximal to branch vessel 12.

As shown in FIG. 5B, an embodiment 26 of an intraluminal device of the invention, comprising a catheter 28 on which is positioned a directionally-expandable angioplasty balloon 30 configured for directional expansion is guided within trunk vessel 10 along guidewire 22, until proximity with plaque lesion 24.

As shown in FIG. 5C, angioplasty balloon 30 is then directionally expanded from distal end 32 to proximal end 34.

As shown in FIG. 5D, the distal to proximal expansion of intraluminal device 26 causes plaque 24 to be pushed sideways and backwards along the inner luminal wall of trunk vessel 10, such that little if any plaque 24 is displaced towards branch vessel 12.

It should be noted that FIGS. 5A to 5D illustrate an exemplary operation in which expansion occurs in a distal to proximal direction. Similar principles apply in the case of proximal to distal, center to side and side to center directional expansions, and may be applied as required according to the relative locations of the plaque lesion and the side branch of the bifurcated vessel.

In some embodiments of the invention, the intraluminal device comprises an asymmetrical-balloon catheter having an asymmetrical balloon configured for directional expansion. In some embodiments the asymmetrical balloon of the asymmetrical-balloon catheter has a first end and a second end, wherein the second end is more tapered than the first end. In some embodiments the distal end of the balloon is the second, more tapered end and the proximal end is the first end. In some embodiments the proximal end of the balloon is the second, more tapered end and the distal end is the first end. In some embodiments, the first, less tapered end has a substantially rectangular cross section. As a result, when expansion fluid is introduced into the balloon, expansion of the balloon begins from the second and proceeds back towards the first end. In some embodiments, the balloon material at the second, more tapered end, is thinner than that at the first, less tapered end, thus provides less resistance to expansion.

The balloon material may comprise any material known in the art for use in manufacture of balloon catheters. Typically, balloons of balloon catheters such as of the asymmetric-balloon catheter described herein are configured for inflation to a diameter of at least five to six times the uninflated diameter. Other desirable properties of balloons for balloon catheters include strength, softness and flexibility which are important for achieving the performance characteristics of folding in an uninflated state, properties of burst strength, compliance, and fatigue. Examples of polymeric materials that are known to be suitable for making balloons for balloon catheters include elastomeric silicone, elastomeric polyurethane and other materials including polyethylenes, polyolefins, polyvinyl chlorides, polyesters, polyimides, polyethylene terephthalates (PET), polyamides, nylons, and the like. In some embodiments, a symmetrical balloon (as known in the art) is fashioned into an asymmetrical balloon as described above by encircling the desired first (proximal or distal) end of the balloon with a band of material that is resistant to radial expansion. As a result, the second (non-encircled) end of the balloon is more tapered and is less resistant to expansion than the first (encircled) end of the balloon that has a substantially rectilinear cross section.

Figure 6:
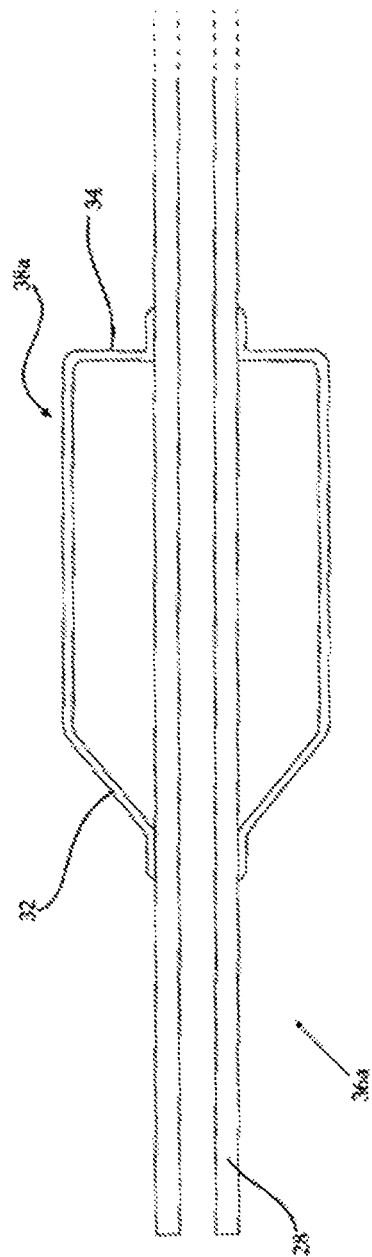
FIGS. 6A and 6B depict a first specific embodiment of the invention, asymmetrical angioplasty balloon configured to directionally expand from a first end to a second end.
Figure 6:
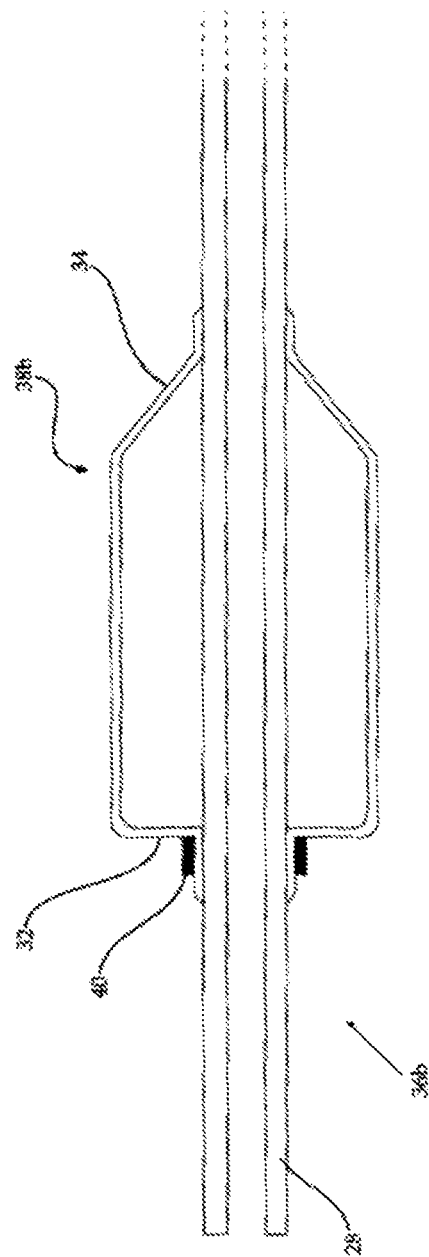

In FIG. 6 embodiments of an intraluminal device of the invention, asymmetrical-balloon catheters 34, having an asymmetrical angioplasty balloon 36 configured for directional expansion, are depicted where the balloons 36 are in an inflated state. Angioplasty balloons 36 are asymmetric, having a less tapered first end (having a substantially rectangular cross section) and a more tapered second end. As a result, when an inflation fluid is introduced into a balloon 36, the balloon 36 inflates from the more tapered end towards the less tapered end, substantially as described with reference to FIG. 5. In FIG. 6, the less-tapered ends of balloons 36 have a substantially rectilinear cross section.

In FIG. 6A, asymmetrical angioplasty balloon 38a of balloon catheter 36a has a more tapered distal end 32 and a less tapered proximal end 34. Balloon 38a of balloon catheter 36a is fabricated having the depicted asymmetrical shape.

In FIG. 6B, asymmetrical angioplasty balloon 38b of balloon catheter 36b has a more tapered proximal end 34 and a less tapered distal end 32. Balloon 38b of balloon catheter 36b is substantially a symmetrical angioplasty balloon around which distal end a constricting band 40 (e.g., a substantially non-expandable material such as high-density polyethylene (HDPE)) is placed.

In some embodiments, the walls of the more tapered end of an asymmetrical angioplasty balloon such as 38 are optionally of a thinner material than of the less tapered end. In some embodiments, the intraluminal device comprises a symmetrical-balloon catheter having a symmetrical balloon configured for directional expansion. In some embodiments the symmetrical balloon of the symmetrical balloon catheter has two substantially equally tapered ends, wherein the thickness of the balloon material is greater at a first end than at a second end, such that greater resistance to expansion is provided at the first end. As a result, when fluid is introduced into the balloon, the balloon expands from the second end towards the first end. In some embodiments the distal end of the balloon is the second, thinner material end and the proximal end is the first end. In some embodiments the proximal end of the balloon is the second, thinner material end and the distal end is the first end. In some embodiments, the thickness of the balloon material is greater at the two ends than near a central section so that the ends have a greater resistance to expansion than the central section. As a result, when fluid is introduced the balloon expands from near the central section outwards towards the ends. In some embodiments, the thickness of the balloon material is greater near a central section than at the two ends so that the central section has a greater resistance to expansion than the ends. As a result, when fluid is introduced the balloon expands from the ends inwards towards the central section.

Referring now to FIGS. 7A to 7C, there is depicted an embodiment 42 of an intraluminal device of the invention comprising catheter 28 and a symmetrically-tapered angioplasty balloon 44. In balloon 44, a first end (in this embodiment, distal end 32) of a thinner material than that of a second end (in this embodiment, proximal end 34). In FIG. 7A, balloon 44 is in an uninflated state. As shown in FIG. 7B, when expansion fluid is introduced into balloon 44, less resistance to expansion is encountered at thinner end distal end 32, such that expansion is directional, from distal end 32 towards proximal end 34, until balloon 44 is fully expanded, FIG. 7C.

In some embodiments (not depicted), a stent is mounted on balloon 44 of device 42. When inflation fluid is introduced into balloon 44 causing balloon 44 to directionally expand from distal end 32 towards proximal end 34, the stent also expands directionally.

In some embodiments, a stent is crimped onto an asymmetrical or symmetrical balloon of a balloon catheter as described above, allowing directional expansion of the stent as a result of the directional expansion of the balloon of the balloon catheter. During deployment, expansion of the balloon begins at a thinner material part or more tapered end and proceeds towards a thicker material part or less tapered end. As a result, the stent radially expands directionally.

Figure 8:
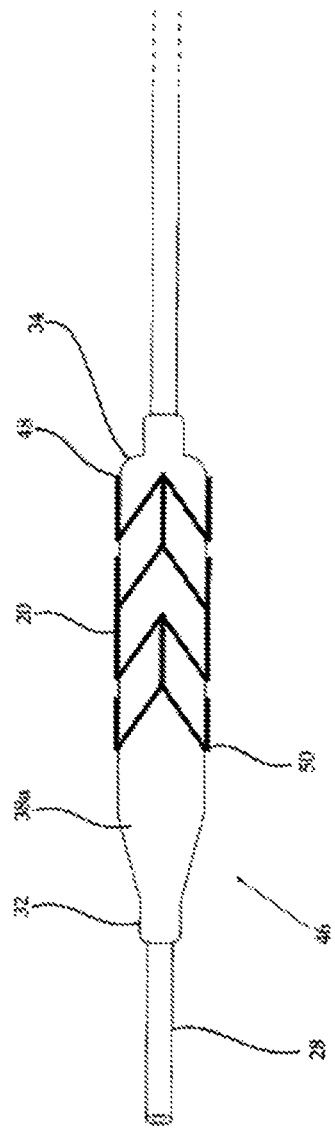
FIGS. 8A and 8B depict stages of the directional expansion of a balloon-expandable stent mounted on an asymmetrical angioplasty balloon.
Figure 8:
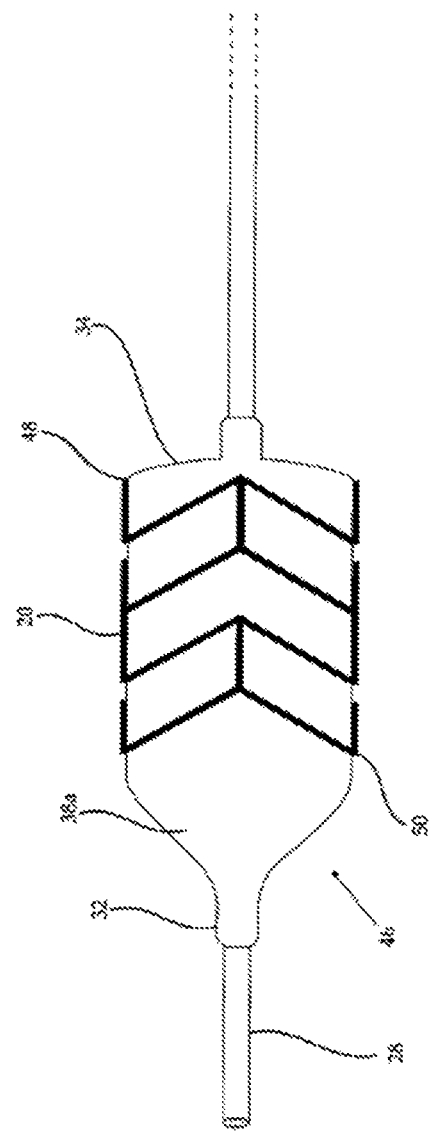

An embodiment of a balloon-expandable stent mounted on a directionally-expandable balloon of a balloon-catheter in accordance with the teachings of the invention and subsequent directional deployment of the stent is depicted in FIG. 8, and described in greater detail below. In some embodiments, the stent is crimped onto the balloon so that the second end of the balloon is not within the stent to ensure that the stent does not cause any resistance to expansion that may prevent a first expansion of the second end.

Substantially any balloon-expandable stent known in the art may be crimped onto a directionally-expandable balloon as described herein including, as noted above, bare-metal stents, drug-eluting stents, coated stents and covered stents.

FIGS. 8A and 8B depict an intraluminal device 46, comprising a catheter 28, on which is positioned an asymmetrical balloon 38a having a more tapered distal end 32 and a less tapered proximal end 34. A stent 20 is crimped onto balloon 38a, such that a proximal end 48 of stent 20 is positioned substantially at less tapered proximal end 34, and a distal end 50 of stent 20 is positioned such that at least a portion of more tapered distal end 32 extends beyond distal end 50 of stent 20.

FIG. 8A shows intraluminal device 46 where balloon 38a is in the unexpanded state. Substantially analogously to the depicted in FIG. 5, upon introduction of an inflation fluid into balloon 38a, balloon 38a directionally expands from the more tapered end (in this embodiments, distal end 32), at which less resistance is encountered, and proceeds towards the less tapered end (in this embodiments, proximal end 34). This directional expansion of balloon 38a causes stent 20 to directionally expand from distal end 48 towards proximal end 50 to a fully-expanded state as depicted in FIG. 7B.

In some embodiments, the intraluminal device comprises a stent configured for directional expansion.

As is known, stents are mounted onto a balloon catheter by sliding the stent in a relatively large-radius state over the balloon of a balloon catheter. Subsequently, an inwards radial force is applied to the outer surface of the stent, crimping the stent around the balloon, for example using a stent-crimping device. In some instances, it is known to heat the stent during the crimping process.

Various crimping devices are known in the art. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent. Another conventional stent crimping tool is manufactured by Johnson & Johnson and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn crimps the stent onto the balloon catheter.

In some embodiments, the directionally-expandable intraluminal device of the invention comprises a stent axially-asymmetrically crimped to a balloon catheter, wherein directional expansion of the stent is achieved by varying the crimping force or the crimping temperature used to crimp the stent around the balloon along the length of the stent. In some embodiments, varying the crimping force and/or the crimping temperature along the length of the balloon during the crimping process leads to directional expansion when the stent is expanded by the balloon, for example from the proximal end of the stent to a distal end, from a distal end of the stent to a proximal end, from near the central section of the stent to the ends of the stent or from the ends of the stent towards the central section of the stent.

In some embodiments, a first section of the stent is crimped onto the balloon with a lesser crimping force and/or lower crimping temperature than other sections of the stent. As a result, the first section of the stent has lesser resistance to radial expansion than the other sections of the stent. Subsequently, when fluid is introduced into the balloon, the stent initially expands at the first section and then directionally, away from the first section towards the other sections that are more resistant to expansion. As noted above, in some embodiments the section crimped onto a balloon so as to have a lesser resistance to radial expansion is the distal end of the stent (allowing directional expansion from the distal end towards the proximal end), in some embodiments the proximal end of the stent (allowing directional expansion from the proximal end towards the distal end), in some embodiments both the distal end and the proximal end of the stent (allowing directional expansion from the ends towards the center of the stent) and in some embodiments a center section of the stent (allowing directional expansion from the center towards the ends of the stent).

FIGS. 9A to 9C depict an intraluminal device, substantially a balloon catheter 28 bearing an angioplasty balloon 18 on which is crimped a stent 52 comprising four ring sections 54a, 54b, 54c and 54d. Stent 52 is crimped onto balloon 18 axially-asymmetrically allowing directional expansion. Specifically, each of ring sections 54a-54d is crimped using different crimping conditions: ring section 54a (at distal end 50 of stent 52) is crimped with the lowest force and/or temperature; adjacent ring section 54b is crimped with somewhat higher force and/or temperature than 54a; adjacent ring section 54c is crimped with somewhat higher force and/or temperature than 54b; and adjacent ring section 54d (at proximal end 48 of stent 52) is crimped at a somewhat higher force and/or temperature than 54c. As depicted in FIG. 9B, upon initiation of expansion by introduction of an expansion fluid into balloon 18, less resistance to expansion is encountered at distal end 50 of stent 52 due to the crimping conditions of ring section 54a. As a result expansion of stent 52 as well as of balloon 18 is directional, from a distal end (50, 32) towards a proximal end (48, 34).

In some embodiments, a directionally-expandable intraluminal device of the invention comprises an axially-asymmetrically balloon-expandable stent, wherein the stent is constructed to provide less resistance at the section to be expand first, that is to say, a stent wherein directional expansion of the stent is be achieved by having sections of the stent wall that are less resistant to radial expansion. In some embodiments, this is achieved, for example, by providing a stent having a lesser amount of material at the section to be expanded first, such as fewer struts and/or thinner struts. A person having ordinary skill in the art is able to manufacture such a stent, for example using standard laser-cutting techniques from a tube of suitable material.

In some embodiments, a directionally balloon-expandable stent is constructed having a lesser amount of material at the proximal end of the stent, the amount of material increasing towards the distal end, such that expansion occurs from the proximal end to the distal end of the stent.

In some embodiments, a directionally balloon-expandable stent is constructed having a lesser amount of material at the distal end, the amount of material increasing towards the proximal end, such that expansion occurs from the distal end to the proximal end of the stent.

In some embodiments, a directionally balloon-expandable stent is constructed having a lesser amount of material at the proximal and distal ends, the amount of material increasing towards the center, such that expansion occurs from the ends to the center of the stent.

In some embodiments, a directionally balloon-expandable stent is constructed having a lesser amount of material at or near the center of the stent, the amount of material increasing towards the proximal and distal ends, such that expansion occurs from the center to the ends of the stent.

Figure 10:
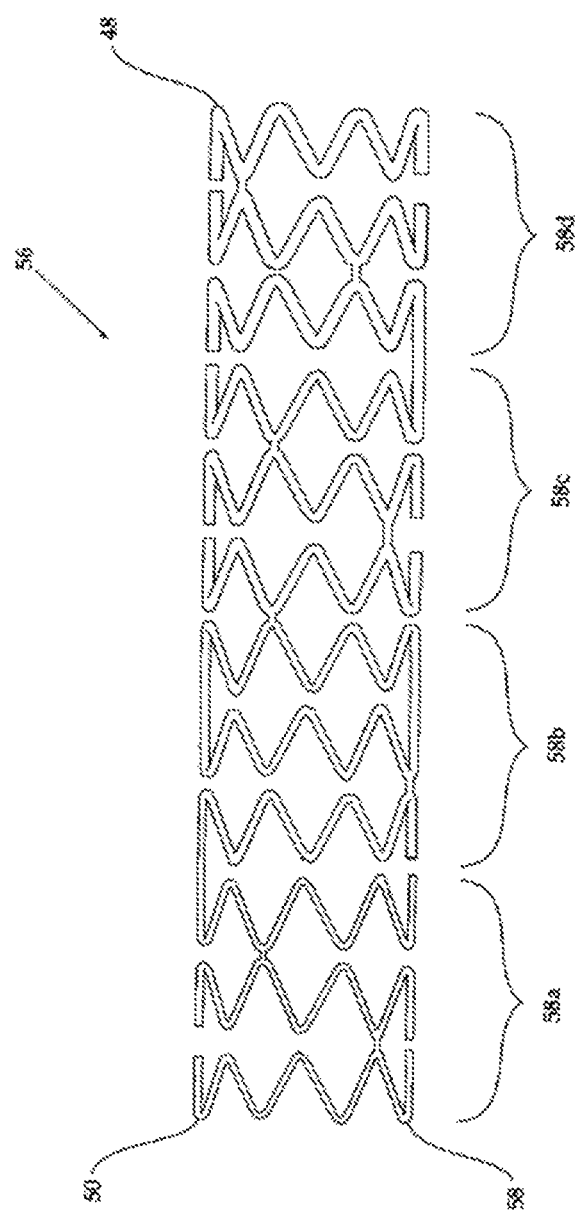
FIG. 10 depicts an embodiment of the invention, a balloon-expandable stent having varying strut thickness and configured to expand from a distal end to a proximal end.

FIG. 10 depicts a balloon-expandable stent 56, similar to a BLAZER® Cobalt Chromium Stent (BLAZER is a registered trademark of OrbusNeich Medical Inc., Fort Lauderdale, Fla., USA), configured for directional expansion in accordance with the teachings herein having a distal end 50 and a proximal end 48. As known in the art, stent 56 is fashioned by laser cutting a tube of an appropriate material exemplified by stainless steel, Nitinol, CoCr alloy, and the like, to leave a framework of struts 58. Struts closer to distal end 50 are progressively narrower while struts 58 closer to proximal end 48 are progressively wider, that is to say the width of struts $58a<58b<58c<58d$. For example, in a specific embodiment where the struts are 0.08 mm thick, struts 58a are 0.09 mm wide, struts 58b are 0.10 mm wide, struts 58c are 0.11 mm wide and struts 58d are 0.12 mm wide. As a result, application of an outwards radial force to the luminal surface of stent 56 leads to directional expansion where the more distal sections of stent 56 defined by struts 58a expand first, and then stent 56 expands directionally from distal end 50 towards proximal end 48.

In FIG. 10, stent 56 is a stent having a framework that substantially comprises rings linked with axial struts. The teachings of the invention are also applicable to stents comprising other types of frameworks.

In some embodiments, the directionally-expandable intraluminal device of the invention comprises an expansion-preventing component located over at least a portion of an external surface of an expandable balloon (with or without a balloon-expandable stent mounted on the balloon), the expansion-preventing component preventing expansion of the expandable balloon at such portions, such that expansion of the balloon is controlled by directional removal of the expansion-preventing element.

In some embodiments, the expansion-preventing element comprises a removable, substantially non-expandable sheath (e.g., of silicone rubber, fluoropolymers, polyethylene terephthalate, polyimide, nylon, polyethylene and the like) around the expandable balloon. The presence of the sheath prevents expansion of the sections of the expandable balloon on which it is located. Gradual directional removal of the sheath allows directional expansion of the expandable balloon in the direction in which the sheath is removed.

In some embodiments, the sheath is analogous to sheaths known in the art of self-expanding stents, covering the balloon and if present, a balloon-expandable stent mounted on the balloon. During use of the intraluminal device, the sheath is partially removed by withdrawing the sheath in a proximal direction, exposing the distal end of the balloon. Fluid is introduced into the balloon leading to expansion of only the exposed distal end of the balloon. The sheath is withdrawn further (gradually or at once, depending on the nature of the balloon) so that further inflation of the balloon (and mounted stent) leads to directional expansion, from the distal end towards the proximal end.

In some embodiments, the sheath is located between the expandable balloon and a balloon-expandable stent, that is to say the stent is crimped over the expandable balloon and sheath. In such embodiments, the sheath is withdrawn distally from between the stent and the balloon.

In some embodiments, the sheath may be pushed forward towards the distal end, such that expansion occurs in a proximal to distal direction.

In some embodiments, the expansion-preventing element further comprises one or more markers visible with a medical imaging modality to enable controlled removal of the sheath. Examples of suitable markers include those visible in one or more of Ultrasound, X-ray, CT, and MRI imaging modalities.

FIGS. 11A and 11B depict an intraluminal device 60 comprising catheter 28, an angioplasty balloon 18, and an externally-placed expansion-preventing element 62 (a sheath, similar to sheaths known in the art of self-expanding stents) placed along at least a portion of the external surface of balloon 18, that initially prevents any expansion of balloon 18, FIG. 11A. Expansion-preventing element 62 is provided with a marker 64 at a distal end thereof.

For use, device 60 is maneuvered in the usual way, for example along a guidewire, to a treatment location. A distal end 32 of angioplasty balloon 18 is positioned as desired in proximity of a lesion with reference to markers 64. Inflation fluid is introduced into balloon 18 while expansion-preventing element 62 is gradually withdrawn in a proximal direction. As depicted in FIG. 11B, distal end 32 of balloon 18 expands first. As additional inflation fluid is introduced into balloon and expansion-preventing element 62 is proximally withdrawn, balloon 18 directionally expands in accordance with the teachings herein. In some embodiments, subsequent to an initial proximal withdrawing allowing distal end 32 of balloon 18 to expand, expansion-preventing element 62 is driven in a proximal direction by further expansion of balloon 18.

In some related embodiments (not depicted), a stent is mounted on a balloon 18 of a device such as 60. When inflation fluid is introduced into the balloon 18 and the expansion-preventing element 62 withdrawn, allowing the balloon 18 to directionally expand from distal end 32 towards proximal end 34, the stent mounted on the balloon 18 also expands directionally.

In some embodiments, the expansion-preventing element is a longitudinal coil placed along an outer surface of the intraluminal device, the coil configured to require a varying amount of force along its length to expand, such that varying resistance is provided to opening of the device. As for previous embodiments, the resistance may be greater at the proximal end, such that expansion of the intraluminal device occurs from the distal to the proximal end; or may be greater at the distal end, such that opening occurs from the proximal to the distal end.

In some embodiments, the expansion-preventing element is a directionally frangible element, such as an appropriately configured collection of one or more sutures, bands or sleeves. In some such embodiments, expansion of the device commences when fluid is introduced into the expandable balloon in sections of the device which are devoid of the expansion-preventing element or in more frangible sections thereof. As a section of the balloon expands, adjacent sections of the balloon are released from the expansion-preventing element (e.g., the element tears or breaks). In some embodiments, the expansion-preventing element includes weak points to ease and direct how the balloon is released.

FIGS. 12A-12C depict an intraluminal device 66 comprising an angioplasty balloon 68 including a distal end 32 and a proximal end 34 mounted on a catheter 28. Surrounding approximately one-third of balloon 68 from distal end 32 is a frangible expansion-preventing element, a sheath 70a made of cellulose including line of perforations 72a. Surrounding approximately one-third of balloon 68 from proximal end 34 is a frangible expansion-preventing element, a sheath 70b made of cellulose including line of perforations 72b. The central section 74 of balloon 68 is not covered by portions of sheath 70.

In FIG. 12A, device 66 is depicted inside a trunk vessel 10 having deposits of plaque 16 where balloon 68 is positioned across an ostium of a branch vessel 12.

Inflation fluid is introduced into balloon 68. As depicted in FIG. 12B, balloon 68 expands where there is least resistance, that is to say central section 74 that is devoid of sheaths 70a and 70b. Lines of perforations 72a and 72b constitute weak points of sheaths 70a and 70b, so that expansion of balloon 68 leads to progressive tearing of sheaths 70a and 70b from central section 74 towards ends 32 and 34 along the perforations 72a and 72b.

Balloon 68 expands from center section 74 outwards towards distal end 32 and proximal end 34, pushing plaque 24 away from branch vessel 12. When balloon 68 is fully expanded, FIG. 12C, trunk vessel 10 is dilated and branch vessel 12 remains substantially unobstructed by plaque.

In some embodiments (not depicted), a stent is mounted on a balloon such as 68 of a device such as 66. When inflation fluid is introduced into the balloon 68, the stent also directionally expands from the center outwards to the distal and proximal ends.

In some embodiments, the expansion-preventing element is a degradable element, such as a degradable suture or band. In some such embodiments, expansion commences in sections of the device which are devoid of the expansion-preventing element, and proceed into the previously constricted segments as the expansion-preventing element degrades. The degradable element may degrade, for example, as a result of heat, blood flow, enzymatic breakdown, pH-related degradation, etc.

The teachings of the present invention are generally applicable to many different cardiovascular and non-cardiovascular applications. Specific cardiovascular applications include but are not limited to the deployment of an intraluminal device of the present invention in narrowed arteries, ectatic arteries and ectatic arteries containing an obstructive lesion, aneurismatic arteries, saphenous vein grafts and native arteries, coronary perforation, coronary fistula, ostial coronary lesions, aortic abdominal aneurysm and other aneurismatic peripheral arteries, transjugular intrahepatic portal shunt, percutaneous transluminal angioplasty, fistula closing and neuro interventions (such as aneurysms and arterial-venous malformations), small vessel intraluminal grafting, and ostial renal artery lesions. Additional non-cardiovascular applications include but are not limited to urological, gastroenterological, respiratory and neurological applications.

In some embodiments, the device or method of the present invention is used in an angioplasty procedure selected from the group consisting of peripheral angioplasty, percutaneous transluminal coronary angioplasty, renal artery angioplasty, carotid angioplasty, and cerebral artery angioplasty.

Aspects of the invention have been described herein primarily with reference to angioplasty of bifurcated vessels, in some embodiments allowing plaque to be directed away from a branch vessel to avoid obstruction thereof.

Although some embodiments of the invention are of great utility in angioplasty treatment of bifurcated vessels, in some embodiments the teachings herein are beneficial for treating non-bifurcated vessels or for other types of treatment. For example, as discussed below, in some embodiments, the teachings herein are beneficial for directing embolic material in a desired direction.

Some embodiments of the invention are used in angioplasty procedures and the like for treating of non-bifurcated blood vessels to direct plaque in a desired direction, for example to a wider portion of a blood vessel.

Some embodiments of the invention are used in angioplasty procedures of blood vessels as a combined angioplasty and embolic protection device. Specifically, a first end of an expandable device expanded blocks a treated blood vessel. The directional expansion of a device of the invention progresses as described hereinabove. Plaque fragments that would be released into the blood vessel using prior art angioplasty methods and that potentially constitute emboli are instead trapped between the expanded first end of the device and the non-expanded surface of the device. As the expansion progresses, the plaque fragments are pressed into, and thereby trapped in, the plaque-mass formed on the luminal surface of the treated vessel.

In related embodiments, the directional expansion of an intraluminal device of the invention is used to detach an embolus or emboli from a blood vessel wall to be captured by a previously deployed embolic protection device, for example during treatment of acute myocardial infarctions, treatment of saphenous vein grafts or of protruding thrombi.

The teachings herein have been discussed in detail relating to intraluminal devices comprising angioplasty balloons and/or balloon-expandable stents. That said, the teachings herein are applicable to other intraluminal devices.

For example, in some embodiments a self-expanding stent is deployed in the usual way in the lumen of a blood vessel including maneuvering to a deployment site in the blood vessel followed by withdrawing of a sheath allowing self-expansion of the self-expanding stent to contact the surface of the plaque deposits. As known in the art, the self-expanding stents apply insufficient force to substantially displace the plaque and in some instances, the struts of the self-expanding stents penetrate into the plaque deposits. Subsequently, a balloon of a balloon-catheter in accordance with the teachings herein is maneuvered into the lumen of the self-expanding stent and directionally expanded in accordance with the teachings herein. As a result, the plaque is directionally displaced, the blood vessel is dilated, and the self-expanding stent is deployed in the blood vessel.

For example, in some embodiments the teachings herein are applied to an expandable stent that serves as a framework for an artificial valve (e.g., a cardiac valve, a mitral valve, an aortic valve, a pulmonary valve, a tricuspid valve) especially an artificial valve configured for percutaneous or transapical deployment. In some such embodiments, an artificial valve is deployed with the use of a directionally-expandable balloon, substantially as described herein. In some such embodiments, the stent that constitutes the expandable framework of the artificial valve is fashioned to be a directionally-expandable stent substantially as described herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. An expandable intraluminal medical device for directional displacement of a lesion within a lumen of a blood vessel, comprising:
 a vascular balloon catheter consisting of an elongate balloon having a tapered end and a substantially rectilinear end conjoined by a central section wherein the substantially rectilinear end is conjoined to the central section at an angle of about 90°, said elongate balloon having one region of decreasing balloon material thickness extending from and including said substantially rectilinear end to and including said tapered end thereby providing a lesser resistance to expansion at said tapered end than at said substantially rectilinear end, such that the elongate balloon is controllably directionally expandable from said tapered end through regions of lesser resistance through regions of greater resistance through to the substantially rectilinear end; and
 a balloon-expandable stent demountably engaged thereon the vascular balloon catheter wherein a proximal end of the stent is positioned at the substantially rectilinear end of the elongate balloon and at least a portion of the tapered end extends beyond a distal end of the stent;
 said device having a proximal end, a distal end, and a central section, wherein said device is configured for controlled directional expansion within the lumen of a blood vessel to thereby controllably displace the lesion toward a selected direction within the lumen of the blood vessel from the tapered end to the substantially rectilinear end of the device, wherein said lesion is one of a plaque or a thrombus or thrombi or combinations thereof.

2. The device of claim 1, wherein the tapered end of the balloon comprises said distal end, such that the resistance to the controlled directional expansion increases from said distal end to the proximal end and said directional expansion is from said distal end towards said proximal end.

3. The device of claim 1, wherein the tapered end of the balloon comprises said proximal end, such that the resistance to the controlled directional expansion increases from said proximal end to said distal end and said expansion is from said proximal end towards said distal end.

4. The device of claim 1, wherein the balloon-expandable stent comprises a lesser amount of material at a section to be expanded first, wherein said lesser amount of material has fewer stent struts or has thinner stent struts.

5. The device of claim 4, wherein said lesser amount of material is situated at the proximal end of the device and increases towards the distal end of the device, such that expansion of said stent occurs from said proximal end towards said distal end; or
 wherein said lesser amount of material is situated at said distal end and increases towards said proximal end, such that expansion of said stent occurs from said distal end towards said proximal end.

6. The device of claim 1, additionally comprising an externally placed expansion-preventing element slid thereon.

7. The device of claim 6, wherein said externally placed expansion-preventing element comprises a removable, non-expandable sheath.

8. The device of claim 6, wherein said externally placed expansion-preventing element is removed from the device placed therein by pulling from a distal end towards a proximal end of said balloon-expandable stent thereby enabling an expansion of the balloon-expandable stent from its distal end to its proximal end, or by pushing from said proximal end towards said distal end of said device, such that expansion occurs from said proximal end to said distal end.

9. The device of claim 6, wherein said externally placed expansion-preventing element comprises one or more markers visible with one or more of ultrasound, X-ray, CT, and MRI imaging modalities.

* * * * *